United States Patent [19]
Koppel

[11] 4,008,230
[45] Feb. 15, 1977

[54] PROCESS FOR PREPARING 3-HYDROXY CEPHALOSPORINS

[75] Inventor: Gary A. Koppel, Indianapolis, Ind.

[73] Assignee: Eli Lilly and Company, Indianapolis, Ind.

[22] Filed: Oct. 29, 1975

[21] Appl. No.: 626,684

[52] U.S. Cl. .............................. 260/243 C; 424/246
[51] Int. Cl.$^2$ ........................................ C07D 501/02
[58] Field of Search ............................... 260/243 C

[56] References Cited

UNITED STATES PATENTS 3,917,588  11/1975  Chauvette .................... 260/243 C Primary Examiner—Nicholas S. Rizzo
Attorney, Agent, or Firm—William C. Martens, Jr.; Everet F. Smith

[57] ABSTRACT

3-Hydroxycephalosporins are prepared by treating a 3-hydroxy-4-bromo-2-(2-formylthio-4-oxo-3-amido or imido-1-azetidinyl)-2-butenoate ester with mercuric acetate and contacting the resulting reaction mixture with a mercuric ion precipitator.

11 Claims, No Drawings

PROCESS FOR PREPARING 3-HYDROXY CEPHALOSPORINS

BACKGROUND OF THE INVENTION

This invention relates to a new process for the preparation of 3-hydroxycephalosporins. These compounds are disclosed and claimed in copending application Ser. No. 310,191 filed Nov. 28, 1974, now Pat. No. 3,917,587. The process disclosed in the copending application for preparing 3-hydroxycephalosporins involves treatment of a 3-exomethylenecepham compound with ozone to form an intermediate ozonide followed by decomposition of the ozonide in the presence of a reducing compound to produce the desired 3-hydroxycephalosporin.

The novel process for preparing 3-hydroxycephalosporins by this invention comprises ring-closure of 3-hydroxy-4-bromo-2-(2-formythio-4-oxo-3-amido-1-azetidinyl)-2-butenoate esters or their corresponding 3-imido compounds. These compounds are alternatively named as azetidinones and, as such, can also be called 1-(1-protected carboxy-2-hydroxy-3-bromo-1-propenyl)-3-amido(or imido)-4-formylthioazetidin-2-ones.

The ring-closure reaction described herein is accomplished by treating the above butenoate esters with mercuric acetate.

SUMMARY OF THE INVENTION

This invention relates to a process for preparing a 3-hydroxycephalosporin of the formula

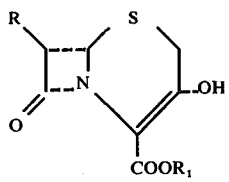

which comprises reacting a butenoate ester compound of the formula

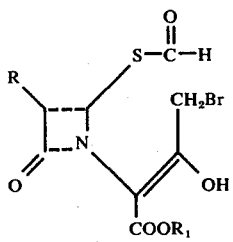

with mercuric acetate in an inert solvent medium, and adding a mercuric ion precipitator to the resulting reaction mixture, in which, in the above formulae, $R_1$ is a carboxylic acid protecting group, and R is a. phthalimido;
b. an amido group of the formula

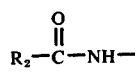

in which $R_2$ is 1. hydrogen, $C_1$–$C_3$ alkyl, halomethyl, thienyl-2-methyl, 4-protected-amino-4-protected carboxybutyl, benzyloxy, 4-nitrobenzyloxy, t-butyloxy, 2,2,2-trichloroethoxy, 4-methoxybenzyloxy;
2. a group of the formula $R'-(O)_m-CH_2-$ in which m is 0 or 1, and R' is phenyl or phenyl substituted with 1 or 2 halogens, protected hydroxy, nitro, cyano, trifluoromethyl, $C_1$–$C_4$ alkyl, or $C_1$–$C_2$ alkoxy;
3. a group of the formula

in which R' is as defined above and W is protected hydroxy, protected carboxy, or protected amino; or
c. an imidazolidinyl group of the formula

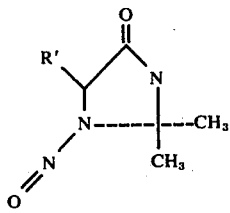

in which R' is as defined above.

DETAILED DESCRIPTION OF THE INVENTION

As delineated hereinabove, the process of this invention is directed to the preparation of 3-hydroxycephalosporins of the formula

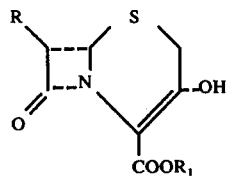

from compounds of the formula

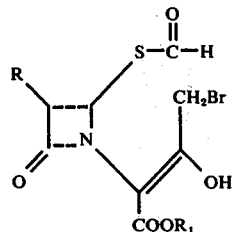

$R_1$ in the above formulae denotes a carboxylic acid protecting group, and, preferably, one which is removable by acid treatment or by hydrogenation. Preferred carboxylic acid protecting groups include, for example, $C_4$–$C_6$ tertalkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$ alkanoyloxymethyl, phenacyl, or p-halophenacyl, in any of the above of which halo denotes chlorine, bromine, or iodine.

Specific illustrations of the preferred carboxylic acid protecting groups which can be employed in the process of this invention include, for example, t-butyl, t-amyl, t-hexyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred carboxylic acid protecting groups are t-butyl, benzyl, p-nitrobenzyl, p-methoxybenzyl, benzhydryl, and 2,2,2-trichloroethyl.

R represents the substituent which is present in the 7-position of the 3-hydroxycephalosporin product of the process of this invention. R can be any of three possibilities or classes of possibilities. Of course, the structure of the R group in the 3-hydroxycephalosporin prepared by the process of this invention will depend upon and be identical to the structure of R in the 3-position of the azetidinyl moiety of the 2-butenoate ester starting material, which, in turn, normally will correspond to the structure of its usual precursor, a matter which is developed hereinafter.

First, R is an imido function, specifically phthalimido.

Secondly, R is an amido function of the formula

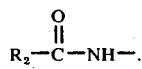

Specific illustrations of the group $R_2$ include for example, hydrogen, methyl, ethyl, n-propyl, isopropyl, chloromethyl, bromomethyl, thienyl-2-methyl, 4-acetamido-4-p-nitrobenzyloxycarbonylbutyl, benzyloxy, 4-nitrobenzyloxy, t-butyloxy, 2,2,2-trichloroethoxy, 4-methoxybenzyloxy, benzyl, 3-bromobenzyl, 2,5-dichlorobenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-ethoxybenzyl, phenoxymethyl, 3-iodophenoxymethyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 3-nitrophenoxymethyl, 4-cyanophenoxymethyl, 2-trifluoromethylphenoxymethyl, 3-methylphenoxymethyl, 4-n-propylphenoxymethyl, 4-n-butylphenoxymethyl, 3-methoxyphenoxymethyl, 4-ethoxyphenoxymethyl, α-benzhydryloxybenzyl, α-(4-methoxybenzyloxy)benzyl, α-(2,2,2-trichloroethoxycarbonylamino)benzyl, α-(benzyloxy)-4-bromobenzyl, α-(benzhydryloxycarbonyl)-3-chlorobenzyl, α-(4-nitrobenzyloxycarbonylamino)-4-fluorobenzyl, α, 4-di(formyloxy)benzyl, α-(4-nitrobenzyloxycarbonyl)-3-chloroacetoxybenzyl, α-(4-methoxybenzyloxycarbonylamino)-4-benzhydryloxybenzyl, α-benzyloxy-3-nitrobenzyl, α-(4-nitrobenzyloxycarbonyl)-2-cyanobenzyl, α-(t-butyloxycarbonylamino)-4-trifluoromethylbenzyl, α-formyloxy-4-methylbenzyl, α-benzyloxycarbonyl-3-n-butylbenzyl, α-(benzyloxycarbonylamino)-4-methoxybenzyl, α-formyloxy-3-ethoxybenzyl, and the like.

Of the above it is highly preferred that R is

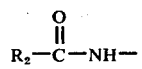

and that $R_2$ thereof is $R'-(O)_m-CH_2-$ in which $R'$ is phenyl.

In portions of the definition provided herein for the group $R_2$, the terms "protected amino", "protected hydroxy", and "protected carboxy" are employed.

The term "protected amino", when employed herein, refers to an amino group substituted with one of the commonly employed amino blocking groups such as t-butyloxycarbonyl (t-BOC), benzyloxycarbonyl, 4-methoxybenzyloxycarbonyl, 4-nitrobenzyloxycarbonyl, 2,2,2-trichloroethoxycarbonyl, diphenylmethoxycarbonyl, isobutyloxycarbonyl, cyclopentyloxycarbonyl, cyclohexyloxycarbonyl, chloroacetyl, dichloroacetyl, 2-chloropropionyl, 3-phenylpropionyl, 4-chlorobutyryl, benzyl, trityl, and the like. Additional typical amino protecting groups are described by J. W. Barton in *Protective Groups in Organic Chemistry*, J. F. W. McOmie, Ed., Plenum Press, New York, N.Y., 1973, Chapter 2. Any of these are recognized as useful within the meaning of the term "protected amino" employed herein.

The term "protected hydroxy", when employed herein, refers to the readily cleavable groups formed with an hydroxyl group such as formyloxy, chloroacetoxy, benzyloxy, benzhydryloxy, trityloxy, 4-nitrobenzyloxy, and the like. Other hydroxy protecting groups, including those described by C. B. Reese in *Protective Groups in Organic Chemistry*, supra, Chapter 3, are considered to be with the term "protected hydroxy" as used herein.

The term "protected carboxy", when employed herein, refers to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrolytic or by hydrogenolytic methods. Any of those groups defined hereinabove for $R_1$ are also included within the meaning of the term "protected carboxy". Examples of carboxylic acid protecting groups include t-butyl, benzyl, 4-methoxybenzyl, $C_2-C_6$ alkanoyloxymethyl, 2-iodoethyl, 4-nitrobenzyl, diphenylmethyl (benzhydryl). phenacyl, p-halophenacyl, 2,2,2-trichloroethyl, succinimidomethyl, and like ester forming moieties. The nature of such ester forming groups is not critical; it is preferred, however, that the ester formed therewith be stable under the reaction conditions of the process of this invention. Futhermore, other known carboxy protecting groups such as those described by E. Haslam in *Protective Groups in Organic Chemistry*, supra, Chapter 5, are considered to be within the term "protected carboxy" as used herein.

Preferred groups within the term "protected carboxy" are tert-butyl, 4-methoxybenzyl, 4-nitrobenzyl, benzhydryl, and 2,2,2-trichloroethyl.

In the foregoing definitions, hydroxy, amino, and carboxy protecting groups, of course, are not exhaustively described. The purpose of these groups is to protect reactive functional groups during preparation of a desired product. They then are removed without disruption of the remainder of the molecule. Many such protecting groups are well known in the art, and their use is equally applicable in the process of this invention.

In addition, the group R in the process of this invention can be an imidazolidinyl group of the formula

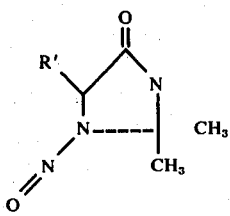

in which R' is phenyl or phenyl substituted with 1 or 2 halogens, protected hydroxy, nitro, cyano, trifluoromethyl, $C_1$–$C_4$ alkyl, or $C_1$–$C_2$ alkoxy.

R' in the above imidazolidinyl formula typically includes phenyl, 3-bromophenyl, 2-chlorophenyl, 4-fluorophenyl, 3-iodophenyl, 3-chloro-4-fluorophenyl, 2-chloro-4-bromophenyl, 4-formyloxyphenyl, 3-formyloxyphenyl, 4-nitrophenyl, 2-cyanophenyl, 3-trifluoromethylphenyl, 4-methylphenyl, 3-ethylphenyl, 4-isopropylphenyl, 4-t-butylphenyl, 3-methoxyphenyl, 2-ethoxyphenyl, 4-methoxyphenyl, and the like.

Compounds in which R is the aforedescribed imidazolidinyl group can be prepared in accordance with known techniques by reacting a compound in which R is

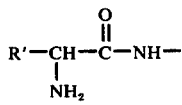

with acetone under moderately basic conditions to produce the corresponding compound in which R is a labile intermediate of the formula

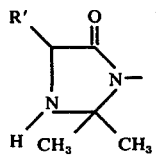

This product then is converted to the stable N-nitroso derivative in which R is the aforedescribed imidazolidinyl group. The latter conversion is accomplished by treatment of the intermediate with sodium nitrite under acidic conditions and with cooling.

In the process of this invention the 3-hydroxy cephalosporins are prepared by ring-closure of a butenoate ester of the formula

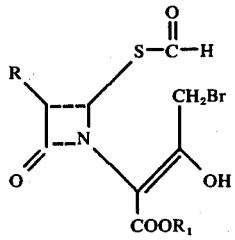

The butenoate ester starting materials are available by reaction of the corresponding 3-bromomethyl-$\Delta^2$-cephem compounds of the formula

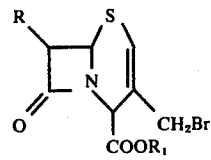

with ozone to form an intermediate ozonide which then is decomposed to the butenoate ester by treatment with a mild reducing agent. The 3-bromomethyl-$\Delta^2$-cephem compounds, in turn, are available from the process disclosed in the Webber et al. U.S. Pat. No. 3,637,678 by reaction of a 3-methyl-$\Delta^2$-cephem with N-bromosuccinimide. Stated more particularly, a 7-amido (or imido)-3-bromomethyl-2-cephem-4-carboxylic acid ester is ozonolyzed by reaction with ozonized oxygen to form an intermediate ozonide at the $C_2$–$C_3$ double bond of the $\Delta^2$-cephem. Treatment of the oxonide so formed with a mild reducing agent effects decomposition of the ozonide and provides the butenoate ester starting material corresponding in structure to the 3-bromomethyl-$\Delta^2$-cephem precursor. The ozonolysis of the 3-bromomethyl-$\Delta^2$-cephem generally is carried out by passing ozonized oxygen gas through a solution of the 3-bromomethyl-$\Delta^2$-cephem in an inert solvent. The reaction generally is carried out at a temperature below about 0° C., and typically at a temperature of from about $-100°$ C. to about $-40°$ C. Of those reactive moieties of the $\Delta^2$-cephem, the $C_2$–$C_3$ double bond preferentially reacts with the ozone to form, in situ, an intermediate ozonide. Generally, the ozonide is not isolated; instead, it is decomposed while in the reaction mixture to provide the butenoate ester. At least a stoichiometric amount of ozone gas generally is employed, although a moderate excess of the ozone, typically an excess of from about 0.1 to about 1 on a molar basis, can be utilized if desired. A large excess of ozone should be avoided, however, since over-oxidation of the cephem can occur. For example, the sulphur atom of the cephem ring system can react with the ozone to form the corresponding sulfoxide. Although sulfoxide formation can occur in the presence of a large excess of ozone, such oxidation proceeds at a very slow rate, and, thus, reaction of the $C_2$–$C_3$ cephem double bond with ozone occurs preferentially and usually proceeds very rapidly. The progess of the ozonolysis reaction generally is monitored to determine the relative amounts of the starting 3-bromomethyl-$\Delta^2$-cephem and the corresponding ozonide product present in the reaction mixture. For instance, the progress of the desired oxidation can be monitored chromatographically by withdrawing an aliquot portion of the reaction mixture, decomposing the intermediate ozonide by adding to the aliquot portion an amount of a mild reducing agent, and chromatographing the aliquot solution by thin layer chromatography. The amount of unreacted 3-bromomethyl-$\Delta^2$-cephem remaining in the reaction mixture can be assessed by comparison of the thin layer chromatogram with that of the amount of 3-bromomethyl-$\Delta^2$-cephem present in an aliquot at the outset of the ozonolysis. The ozonolysis reaction generally is curtailed when no starting $\Delta^2$-cephem remains in the reaction mixture, thereby minimizing the possibilities for over-oxidation. Generally, the ozonolysis is substantially completed within 1 to 5 hours. As hereinbefore indicated, the ozonolysis reaction is best conducted in an inert solvent. Any of a number of inert solvents can be employed for the reaction. Commonly used inert solvents include the halogenated hydrocarbons, such as chloroform, dichloromethane, fluorotrichloromethane, 1,2-dichloroethane, dichlorodifluoromethane, 1,1-dichloroethane, bromoethane, carbon tetrachloride, and the like. Additionally, ethers such as diethyl ether, petroleum ether, tetrahydrofuran, diethylene glycol dimethyl ether, methyl ethyl ether, and related ethers are suitable inert solvents. Similarly, solvents such as hexane, dimethylformamide, dimethylacetamide, ethyl acetate, methyl acetate, water, acetic acid, and the like, can be employed in the ozonolysis reaction.

Upon completion of the ozonolysis reaction, as evidenced, for example, by the lack of any 3-bromomethyl-$\Delta^2$-cephem remaining in the reaction mixture as shown by thin layer chromatographic analysis, any excess ozone remaining in the reaction mixture generally is removed by purging the reaction mixture with nitrogen or oxygen gas. The ozonide intermediate which is formed by ozonolysis of the $\Delta^2$-cephem need not be isolated; instead, it is decomposed by reaction with a mild reducing agent to provide the butenoate ester starting material.

The term "mild reducing agent" refers to any reducing agent capable of decomposing the ozonide intermediate while at the same time not affecting other sites of the ozonide molecule. For example, the reducing agent must not hydrolyze the azetidinone ring system of the butenoate ester under the reaction conditions being used. Mild reducing agents which are commonly used to decompose ozonides are well known, and include such agents as zinc or magnesium and water or acetic acid, sodium bisulfite, sulfur dioxide, trimethyl phosphite, stannous chloride, zinc metal dust, Raney nickel, and the like. The decomposition of the intermediate ozonide normally is accomplished by adding an excess of the reducing agent to the reaction mixture maintained at a temperature of from about −80° C. to about 0° C. and stirring the mixture. The ozonide decomposition generally is completed within about 1 to 3 hours. Progress of the decomposition can be monitored by periodically treating a sample of the reaction mixture with a potassium iodide-starch mixture.

The butenoate ester typically is isolated by washing the reaction mixture with water, separating the organic phase, and concentrating it to dryness. The product can be further purified, if desired, by any of a number of commonly used purification techniques, including column chromatography, gas chromatography, recrystallization, and related methods.

It, of course, will understood by those skilled in the art of organic chemistry that the butenoate ester starting materials are enols and exist in tautomeric equilibrium with the corresponding 1,3-dicarbonyl ketone. The tautomeric equilibrium can be illustrated by the following generalized scheme:

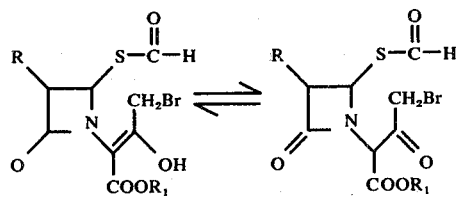

As a result of the existence of this tautomeric equilibrium, the keto form of the molecule will be understood to be included in the definition of the butenoate ester starting material.

In carrying out the process of this invention, the butenoate ester typically is mixed with at least a molar equivalent of mercuric acetate and preferably from about a molar equivalent to about a 10 percent excess on a molar basis of the mercuric acetate relative to the butenoate ester. A larger excess of mercuric acetate can be employed; however, the presence of a larger excess does not provide any significant advantage.

The butenoate ester and the mercuric acetate are dissolved in a suitable inert solvent medium. Although any of a host of solvents can be employed from the standpoint of inertness to the ring-closure, it is highly preferred that the reaction be carried out under conditions which afford dissolution both of the butenoate ester and of the mercuric acetate. Typically, therefore, the solvent medium will comprise a mixture of solvents, at least one of which will promote solubilization of the mercuric acetate and at least another of which will promote solubilization of the butenoate ester. Preferably, therefore, aprotic inert organic solvents, such as aromatic hydrocarbons, for example, benzene, toluene, and the like; halogenated hydrocarbons, for example, methylene chloride, chloroform, carbon tetrachloride, and the like; or other like aprotic inert solvents, are employed to dissolve the butenoate ester. In combination therewith, it is preferred that a solvent for the mercuric acetate be employed, such as, for example, a $C_1$–$C_4$ carboxylic acid such as formic acid, acetic acid, propionic acid, isobutyric acid, n-butyric acid, and the like. The preferred such solvent is acetic acid. As indicated, a mixture of the two classes of solvents is useful in achieving dissolution of both of the reactants which participate in the ring-closure process of this invention. Preferably, when an aprotic inert organic solvent is employed in combination with a solvent for the mercuric acetate, the amounts of each on a volume basis is from about 1:1 to about 4:1 of the aprotic inert organic solvent relative to the mercuric acetate solvent.

The preparation of a 3-hydroxy cephalosporin in accordance with the process of this invention typically is accomplished by treating the aforedescribed solution of the reactants at a temperature of from about −10° C. to about +25° C., and preferably from about +20° C. to about +25° C. for a period of from about 3 minutes to about 10 minutes. The reaction generally is quite rapid; however, the reaction time can be greatly extended, even to several hours, without substantial loss of or serious detriment to the ultimate 3-hydroxy cephalosporin product which is formed.

In order to accomplish production of the 3-hydroxy cephalosporins in accordance with the process of this invention, it is essential that the reaction mixture which results from the reaction of the butenoate ester and mercuric acetate be treated witn an agent which will precipitate mercuric ion. Such agents are recognized in the art and include, for example, hydrogen sulfide, lower alkyl mercaptans, and the like. Typical such lower alkyl mercaptans include, for example, methyl mercaptan, ethyl mercaptan, n-propyl mercaptan, isopropyl mercaptan, t-butyl mercaptan, isobutyl mercaptan, n-butyl mercaptan, and the like. Preferably, and for the sake of convenience, hydrogen sulfide is employed as mercuric ion precipitator.

Although it is not intended that this invention be limited thereby, it is assumed that the ring closure reaction proceeds by inital formation of a butenoate ester intermediate containing the thio moiety -S-Hg(OAc) in which OAc represents acetate. Ring-closure of this intermediate is accomplished by abstraction of the mercury from the reaction intermediate using a reagent which will precipitate the mercury as an insoluble mercuric salt.

The mercuric ion precipitator therefore should be employed in a quantity sufficient at least to account for all of the mercuric acetate originally added to the reaction mixture. An excess of the mercuric ion precipitator can be employed without serious detriment. Thus, for example, when hydrogen sulfide is employed, it is merely bubbled into the reaction mixture for a period sufficient to ensure the addition of an amount of hydrogen sulfide adequate to account for all of the mercuric ion originally added to the reaction mixture.

Once the mercuric ion precipitator has been added to the reaction mixture and the mercuric compound has been precipitated, the insoluble material is removed, for example, by filtration. In the event that a filtration step is included, it may be desirable to employ a filter aide as well as a decolorizing agent such as activated carbon. The use of the latter is especially preferred in those instances in which the resultant insoluble mercuric compound is mercuric sulfide, since mercuric sulfide is black and tends to discolor the reaction mixture.

The reaction mixture filtrate contains the desired product, the 3-hydroxy cephalosporin, formed by ring-closure of the intermediate by abstraction of the mercuric ion. This product can be recovered simply by evaporation of the reaction mixture solvent. Evaporation generally is carried out in vacuo to avoid excessive heating of the product.

Examples of the conversions which are available from the process of this invention are the following:

t-butyl 3-hydroxy-4-bromo-2-(2-formylthio-4-oxo-3-phthalimido-1-azetidinyl)-2-butenoate to t-butyl 7-phthalimido-3-hydroxy-3-cephem-4-carboxylate; benzyl 3-hydroxy-4-bromo-2-(2-formylthio-4-oxo-3-formamido-1-azetidinyl)-2-butenoate to benzyl 7-formamido-3-hydroxy-3-cephem-4-carboxylate;

2,2,2-trichloroethyl 3-hydroxy-4-bromo-2-(2-formylthio-4-oxo-3-acetamido-1-azetidinyl)-2-butenoate to 2,2,2-trichloroethyl 7-acetamido-3-hydroxy-3-cephem-4-carboxylate.

p-nitrobenzyl 3-hydroxy-4-bromo-2-(2-formylthio-4-oxo-3-butyramido-1-azetidinyl)-2-butenoate to p-nitrobenzyl 7-butyramido-3-hydroxy-3-cephem-4-carboxylate;

p-methoxybenzyl 3-hydroxy-4-bromo-2-(2-formylthio-4-oxo-3-chloroacetamido-1-azetidinyl)-2-butenoate to p-methoxybenzyl 7-chloroacetamido-3-hydroxy-3-cephem-4-carboxylate;

benzhydryl 3-hydroxy-4-bromo-2-[2-formylthio-4-oxo-3-(4'-chloroacetamido-40'-benzhydryloxycarbonylvaleramido)-1-azetidinyl]-2-butenoate to benzhydryl 7-(4'-chloroacetamido-4'-benzhydryloxycarbonylvaleramido)-3-hydroxy-3-cephem-4-carboxylate;

p-nitrobenzyl 3-hydroxy-4-bromo-2-[2-formylthio-4-oxo-3-(4'-nitrobenzyloxycarbamido)-1-azetidinyl]-2-butenoate to p-nitrobenzyl 7-(4'-nitrobenzyloxycarbamido)-3-hydroxy-3-cephem-4-carboxylate;

t-amyl 3-hydroxy-4-bromo-2-(2-formylthio-4-oxo-3-benzyloxycarbamido-1-azetidinyl)-2-butenoate to t-amyl 7-benzyloxycarbamido-3-hydroxy-3-cephem-4-carboxylate; ethyl 3-hydroxy-4-bromo-2-[2-formylthio-4-oxo-3-(t-butyloxycarbamido)-1-azetidinyl]-2-butenoate to ethyl 7-(t-butyloxycarbamido)-3-hydroxy-3-cephem-4-carboxylate;

2-iodoethyl 3-hydroxy-4-bromo-2-[2-formylthio-4-oxo-3-(2',2',2'-trichloroethoxycarbamido)-1-azetidinyl]-2-butenoate to 2-iodoethyl 7-(2',2',2'-trichloroethoxycarbamido)-3-hydroxy-3-cephem-4-carboxylate;

acetoxymethyl 3-hydroxy-4-bromo-2-[2-formylthio-4-oxo-3-(4'-methoxybenzyloxycarbamido)-1-azetidinyl]-2-butenoate to acetoxymethyl 7-(4'-methoxybenzyloxycarbamido)-3-hydroxy-3-cephem-4-carboxylate;

p-methoxybenzyl 3-hydroxy-4-bromo-2-(2-formylthio-4-oxo-3-phenylacetamido-1-azetidinyl)-2-butenoate to p-methoxybenzyl 7-phenylacetamido-3-hydroxy-3-cephem-4-carboxylate;

2,2,2-trichloroethyl 3-hydroxy-4-bromo-2-(2-formylthio-4-oxo-3-phenoxyacetamido-1-azetidinyl)-2-butenoate to 2,2,2-trichloroethyl 7-phenoxyacetamido-3-hydroxy-3-cephem-4-carboxylate;

p-nitrobenzyl 3-hydroxy-4-bromo-2-[2-formylthio-4-oxo-3-(2',5'-dichlorophenylacetamido)-1-azetidinyl]-2-butenoate to p-nitrobenzyl 7-(2',5'-dichlorophenylacetamido)-3-hydroxy-3-cephem-4-carboxylate;

benzyl 3-hydroxy-4-bromo-2-[2-formylthio-4-oxo-3-(3'-bromophenoxyacetamido)-1-azetidinyl]-2-butenoate to benzyl 7-(3'-bromophenoxyacetamido)-3-hydroxy-3-cephem-4-carboxylate;

t-butyl 3-hydroxy-4-bromo-2-[2-formylthio-4-oxo-3-(4'-chloroacetoxyphenylacetamido)-1-azetidinyl]-2-butenoate to t-butyl 7-(4'-chloroacetoxyphenylacetamido)-3-hydroxy-3-cephem-4-carboxylate;

t-hexyl 3-hydroxy-4-bromo-2-[2-formylthio-4-oxo-3-(3'-formyloxyphenoxyacetamido)-1-azetidinyl]-2-butenoate to t-hexyl 7-(3'-formyloxyphenoxyacetamido)-3-hydroxy-3-cephem-4-carboxylate;

p-nitrobenzyl 3-hydroxy-4-bromo-2-[2-formylthio-4-oxo-3-(2'-nitrophenylacetamido)-1-azetidinyl]-2-butenoate to p-nitrobenzyl 7-(2'-nitrophenylacetamido)-3-hydroxy-3-cephem-4-carboxylate;

p-methoxybenzyl 3-hydroxy-4-bromo-2-[2-formylthio-4-oxo-3-(4'-nitrophenoxyacetamido)-1-azetidinyl]-2-butenaote to p-methoxybenzyl 7-(4'-nitrophenoxyacetamido)-3-hydroxy-3-cephem-4-carboxylate;

benzhydryl 3-hydroxy-4-bromo-2-[2-formylthio-4-oxo-3-(3'-cyanophenylacetamido)-1-azetidinyl]-2-butenoate to benzhydryl 7-(3'-cyanophenylacetamido)-3-hydroxy-3-cephem-4-carboxylate;

p-bromophenacyl 3-hydroxy-4-bromo-2-[2-formylthio-4-oxo-3-(2'-cyanophenoxyacetamido)-1-azetidinyl]-2-butenoate to p-bromophenacyl 7-(2'-cyanophenoxyacetamido)-3-hydroxy-3-cephem-4-carboxylate;

propionoxymethyl 3-hydroxy-4-bromo-2-[2-formylthio-4-oxo-3-(4'-trifluoromethylphenylacetamido)-1-azetidinyl]-2-butenoate to propionoxymethyl 7-(4'-trifluoromethylphenylacetamido)-3-hydroxy-3-cephem-4-carboxylate;

2,2,2-tribromoethyl 3-hydroxy-4-bromo-2-[2-formylthio-4-oxo-3-(3'-trifluoromethylphenoxyacetamido)-1-azetidinyl]-2-butenoate to 2,2,2-tribromoethyl 7-(3'-trifluoromethylphenoxyacetamido)-3-hydroxy-3-cephem-4-carboxylate;

2-iodoethyl 3-hydroxy-4-bromo-2-[2-formylthio-4-oxo-3-(2'-ethylphenylacetamido)-1-azetidinyl]-2- butenoate to 2-iodoethyl 7-(2'-ethylphenylacetamido)-3-hydroxy-3-cephem-4-carboxylate;

acetoxymethyl 3-hydroxy-4-bromo-2-[2-formylthio-4-oxo-3-(4'-isopropylphenoxyacetamido)-1-azetidinyl]-2-butenoate to acetoxymethyl 7-(4'-isopropylphenoxyacetamido)-3-hydroxy-3-cephem-4-carboxylate;

t-butyl 3-hydroxy-4-bromo-2-[2-formylthio-4-oxo-3-(3'-ethoxyphenylacetamido)-1-azetidinyl]-2-butenoate to t-butyl 7-(3'-ethoxyphenylacetamido)-3-hydroxy-3-cephem-4-carboxylate;

p-nitrobenzyl 3-hydroxy-4-bromo-2-[2-formylthio-4-oxo-3-(4'-methoxyphenoxyacetamido)-1-azetidinyl]-2-butenoate to p-nitrobenzyl 7-(4'-methoxyphenoxyacetamido)-3-hydroxy-3-cephem-4-carboxylate;

p-nitrobenzyl 3-hydroxy-4-bromo-2-[2-formylthio-4-oxo-3-(α-formyloxyphenylacetamido)-1-azetidinyl]-2-butenoate to p-nitrobenzyl 7-(α-formyloxyphenylacetamido)-3-hydroxy-3-cephem-4-carboxylate;

p-methoxybenzyl 3-hydroxy-4-bromo-2-[2-formylthio-4-oxo-3-(α-benzhydryloxyphenylacetamido)-1-azetidinyl]-2-butenoate to p-methoxybenzyl 7-(α-benzhydryloxyphenylacetamido)-3-hydroxy-3-cephem-4-carboxylate;

benzhydryl 3-hydroxy-4-bromo-2-[2-formylthio-4-oxo-3-(α-benzhydryloxycarbonylphenylacetamido)-1-azetidinyl]-2-butenoate to benzhydryl 7-(α-benzhydryloxycarbonylphenylacetamido)-3-hydroxy-3-cephem-4-carboxylate;

p-nitrobenzyl 3-hydroxy-4-bromo-2-[2-formylthio-4-oxo-3-(α-benzyloxycarbonylaminophenylacetamido)-1-azetidinyl]-2-butenoate to p-nitrobenzyl 7-(α-benzyloxycarbonylaminophenylacetamido)-3-hydroxy-3-cephem-4-carboxylate;

t-butyl 3-hydroxy-4-bromo-2-[2-formylthio-4-oxo-3-(α-t-butyloxycarbonylaminophenylacetamido)-1-azetidinyl]-2-butenoate to t-butyl 7-(α-t-butyloxycarbonylaminophenylacetamido)-3-hydroxy-3-cephem-4-carboxylate;

p-nitrobenzyl 3-hydroxy-4-bromo-2-[2-formylthio-4-oxo-3-(2'-thienylacetamido)-1-azetidinyl]-2-butenoate to p-nitrobenzyl 7-(2'-thienylacetamido)-3-hydroxy-3-cephem-4-carboxylate; and the like.

The 3-hydroxy cephalosporins (3-hydroxycephems) obtained from the process of this invention can be employed in the preparation of cephem antibiotics of the formula

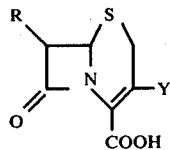

in which Y is, for example, chloro, bromo or methoxy. Such chemical conversions from 3-hydroxy cephalosporin compounds have been disclosed in the chemical literature [Robert R. Chauvette and Pamela A. Pennington, *Journal of the American Chemical Society*, 96, 4986 (1974)].

In general, the 3-hydroxycephems can be treated with diazomethane at room temperature in tetrahydrofuran containing one equivalent of triethylamine to produce the corresponding 3-methoxycephem derivatives. The 3-halocephems are derived from the 3-hydroxycephem esters by treatment with a halogenating reagent such as thionyl chloride or phosphorous tribromide in N,N-dimethylformamide.

The corresponding cephem acids exhibits potent anti-bacterial activity. These are available by cleavage of the ester function. Deesterification can be achieved, depending upon the nature of the protecting group, by any of several recognized procedures, including (1) treatment with an acid such as trifluoroacetic acid, formic acid, hydrochloric acid or the like; (2) treatment with zinc and an acid such as formic acid, acetic acid or hydrochloric acid; or (3) hydrogenation in the presence of palladium, platinum, rhodium or a compound thereof, in suspension, or on a carrier such as barium sulfate, carbon, alumina or the like.

This invention is further illustrated by reference to the examples which follow. It is not intended that this invention be limited in scope by reason of any of the examples provided herein.

EXAMPLE 1

A solution of 1.932 g. (4 mmoles) of t-butyl 7-phenoxyacetamido-3-bromomethyl-2-cephem-4-carboxylate and 100 ml. of $CH_2Cl_2$ was cooled in an acetone-dry ice bath (−78° C.), and ozone was introduced until a blue color appeared (about 3–5 minutes). Sulfur dioxide gas then was passed through the mixture for about 2–5 minutes, and the mixture was allowed to warm to room temperature. An nmr analysis of a sample of the mixture was consistent for the presence of t-butyl 3-hydroxy-4-bromo-2-(2-formylthio-4-oxo-3-phenoxyacetamido-1-azetidinyl)-2-butenoate.

NMR ($CDCl_3$) δ 1.5 (s, t-Bu), 4.1 and 4.3 (dd, J = 12 Hz, $CH_2Br$), 4.53 (s, $CH_2O$), 5.15 and 5.35 (dd, J = 5 Hz), 6.1 (d, J = 5 Hz), 6.8 – 7.3 (m, 5 arom. H), 7.45 (d, NH), 10 (s, CHO), and 12.4 Hz (br. s, OH).

EXAMPLE 2

To 0.391 g. (1.mmol.) of mercuric acetate in a mixture of 15 ml. of methylene chloride and 15 ml. of acetic acid was added, as a neat solid, 0.435 g. (1 mmol.) of t-butyl 3-hydroxy-4-bromo-2-(2-formylthio-4-oxo-3-phenoxyacetamido-1-azetidinyl)-2-butenoate. The resulting mixture was stirred for five minutes at room temperature after which time the solution became cloudy. Hydrogen sulfide was bubbled into the mixture, and the mixture was filtered through a filter aide an charcoal. The filtrate was evaporated to a residue to obtain t-butyl 7-phenoxyacetamido-3-hydroxy-3-cephem-4-carboxylate.

The residue of the 3-hydroxy cephalosporin was dissolved in 10 ml. of N,N-dimethylformamide, and 20 drops of phosphorus trichloride were added. The resulting mixture was stirred for one hour. The mixture then was poured into water, and the aqueous mixture was extracted with ethyl acetate. The resulting product, t-butyl 7-phenoxyacetamido-3-chloro-3-cephem-4-carboxylate, was purified by thick layer chromatography on silica gel eluted with a 7:3 mixture of benzene and ethyl acetate, to obtain 50 mg. of the 3-chlorocephalosporin product. Spectral analyses of the product were consistent with the 3-chlorocephalosporin structure.

ir $\lambda_{max}(CHCl_3)$: 1785, 1735, and 1700 cm$^{-1}$.

nmr ($CDCl_3$) δ 1.6 (s, 9, t-butyl), 314 (broad s, 2, $C_2$-H,), 4.64 (s, 2, phenoxyacetylmethylene), and 5.3–5.9 (m, 2, $C_6$ and $C_7$-H).

EXAMPLE 3

To 0.391 g. (1 mmol.) of mercuric acetate in a mixture of 20 ml. of benzene and 15 ml. of acetic acid are added 0.542 g. (1 mmol.) of 3-hydroxy-4-bromo-2-[2-formylthio-4-oxo-3-(α-formyloxyphenylacetamido)-1-azetidinyl]-2-butenoate, p-nitrobenzyl ester, as a neat solid. The mixture is stirred for 10 minutes at 20° C., after which time the solution becomes cloudy. Hydrogen sulfide is bubbled into the mixture, and the mixture then is filtered through activated charcoal and a filter aide. The resulting filtrate is evaporated, and a residue comprising p-nitrobenzyl 7-(α-formyloxyphenylacetamido)-3-hydroxy-3-cephem-4-carboxylate is obtained.

EXAMPLE 4

To 0.430 g. (1.1 mmol.) of mercuric acetate in a mixture of 20 ml. of toluene and 10 ml. of propionic acid are added 0.632 g. (1 mmol.) of 3-hydroxy-4-bromo-2-[2-formylthio-4-oxo-3-(α-benzyloxycarbonylaminophenylacetamido)-1-azetidinyl]-2-butenoate, p-methoxybenzyl ester, in 20 ml. of toluene. The mixture is stirred for 30 minutes at 15° C., after which time the solution becomes cloudy. Hydrogen sulfide is bubbled into the mixture, and the mixture then is filtered through activated charcoal and a filter aide. The resulting filtrate is evaporated, and a residue comprising p-methoxybenzyl 7-(α-benzyloxycarbonylaminophenylacetamido)-3-hydroxy-3-cephem-4-carboxylate is obtained.

EXAMPLE 5

To 0.410 g. (1.05 mmol.) of mercuric acetate in a mixture of 10 ml. of chloroform and 10 ml. of butyric acid are added 0.529 g. (1 mmol.) of 3-hydroxy-4-bromo-2-(2-formylthio-4-oxo-3-phenylacetamido-1-azetidinyl)-2-butenoate, benzhydryl ester, in 10 ml. of chloroform. The mixture is stirred for 15 minutes at 10° C., after which time the solution becomes cloudy. Ethyl mercaptan is added to the mixture, and the mixture then is filtered through activated charcoal and a filter aide. The resulting filtrate is evaporated, and a residue comprising benzhydryl 7-phenylacetamido-3-hydroxy-3-cephem-4-carboxylate is obtained.

EXAMPLE 6

To 0.782 g. (2 mmol.) of mercuric acetate in 30 ml. of acetic acid are added 0.538 g. (1 mmol.) of 3-hydroxy-4-bromo-2-[2-formylthio-4-oxo-3-(4'-formyloxyphenylacetamido)-1-azetidinyl]-2-butenoate, 2,2,2-trichloroethyl ester, in 30 ml. of methylene chloride. The mixture is stirred for 60 minutes at 5° C., after which time the solution becomes cloudy. Hydrogen sulfide is bubbled into the mixture, and the mixture then is filtered through activated charcoal and a filter aide. The resulting filtrate is evaporated, and a residue comprising 2,2,2-trichloroethyl 7-(4'-formyloxyphenylacetamido)-3-hydroxy-3-cephem-4-carboxylate is obtained.

EXAMPLE 7

To 0.586 g. (1.5 mmol.) of mercuric acetate in a mixture of 30 ml. of carbon tetrachloride and 30 ml. of acetic acid are added 0.457 g. (1 mmol.) of 3-hydroxy-4-bromo-2-[2-formylthio-4-oxo-3-(2'-thienylacetamido)-1azetidinyl]-2-butenoate, benzyl ester, as a neat solid. The mixture is stirred for 7 minutes at 20° C., after which time the solution becomes cloudy. Methyl mercaptan is added to the mixture, and the mixture then is filtered through activated charcoal and a filter aide. The resulting filtrate is evaporated, and a residue comprising benzyl 7-(2'-thienylacetamido)-3-hydroxy-3-cephem-4-carboxylate is obtained.

EXAMPLE 8

To 0.391 g. (1 mmol.) of mercuric acetate in a mixture of 15 ml. of benzene and 10 ml. of propionic acid are added 0.485 g. (1 mmol.) of 3-hydroxy-4-bromo-2-[2-formylthio-4-oxo-3-(3'-chlorophenoxyacetamido)-1-acetidinyl]-2-butenoate, acetoxymethyl ester, as a neat solid. The mixture is stirred for 80 minutes at −10° C., after which time the solution becomes cloudy. Hydrogen sulfide is bubbled into the mixture, and the mixture then is filtered through activated charcoal and a filter aide. The resulting filtrate is evaporated, and a residue comprising acetoxymethyl 7-(3'-chlorophenoxyacetamido)-3-hydroxy-3-cephem-4-carboxylate is obtained.

EXAMPLE 9

To 0.430 g. (1.1 mmol.) of mercuric acetate in a mixture of 30 ml. of methylene chloride and 10 ml. of acetic acid are added 0.582 g. (1 mmol.) of 3-hydroxy-4-bromo-2-[2-formylthio-4-oxo-3-(2',2'-dimethyl-3'-nitroso-5'-oxo-4'-phenylimidazolidin-1'-yl)-1-azetidinyl]-2-butenoate, p-nitrobenzyl ester, as a neat solid. The mixture is stirred for 3 minutes at 25° C., after which time the solution becomes cloudy. Hydrogen sulfide is bubbled into the mixture, and the mixture then is filtered through activated charcoal and a filter aide. The resulting filtrate is evaporated, and a residue comprising p-nitrobenzyl 7-(2',2'-dimethyl-3'-nitroso-5'-oxo-4'-phenylimidazolidin-1'-yl)-3-hydroxy-3-cephem-4-carboxylate is obtained.

EXAMPLE 10

To 0.391 g. (1 mmol.) of mercuric acetate in a mixture of 15 ml. of toluene and 15 ml. of isobutyric acid are added 0.739 g. (1 mmol.) of 3-hydroxy-4-bromo-2-[2-formylthio-4-oxo-3-(α-benzhydryloxycarbonylphenylacetamido)-1-azetidinyl]-2-butenoate, benzhydryl ester, as a neat solid. The mixture is stirred for 20 minutes at 18° C., after which time the solution becomes cloudy. n-Propyl mercaptan is added to the mixture, and the mixture then is filtered through activated charcoal and a filter aide. The resulting filtrate is evaporated, and a residue comprising benzhydryl 7-(α-benzhydryloxycarbonylphenylacetamido)-3-hydroxy-3-cephem-4-carboxylate is obtained.

EXAMPLE 11

To 0.782 g. (2 mmol.) of mercuric acetate in 40 ml. of acetic acid are added 0.544 g. (1 mmol.) of 3-hydroxy-4-bromo-2-[2-formylthio-4-oxo-3-(4'-methoxyphenoxyacetamido)-1-azetidinyl]-2-butenoate, -nitrobenzyl ester, in 30 ml. of methylene chloride. The mixture is stirred for 7 minutes at 23° C. after which time the solution becomes cloudy. Isobutyl mercaptan is added to the mixture, and the mixture then is filtered through activated charcoal and a filter aide. The resulting filtrate is evaporated, and a residue comprising p-nitrobenzyl 7-(4'-methoxyphenoxyacetamido)-3-hydroxy-3-cephem-4-carboxylate is obtained.

I claim:
1. A process for preparing a 3-hydroxycephalosporin of the formula

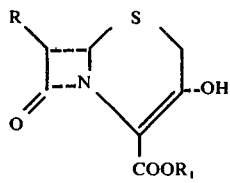

which comprises the step of reacting a compound of the formula

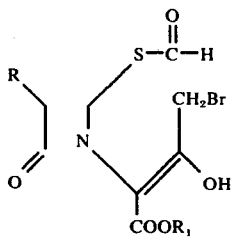

with mercuric acetate in an inert solvent medium, and adding a mercuric ion precipitator to the resulting reaction mixture, in which, in the above formulae, $R_1$ is a carboxylic acid protecting group, and R is a. phthalimido;
b. an amido group of the formula

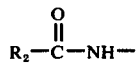

in which $R_2$ is
1. hydrogen, $C_1$–$C_3$ alkyl, halomethyl, thienyl-2-methyl, 4-protected-amino-4-protected carboxybutyl, benzyloxy, 4-nitrobenzyloxy, t-butyloxy, 2,2,2-trichloroethoxy, 4-methoxybenzyloxy;
2. a group of the formula $R'$—$(O)_m$—$CH_2$— in which $m$ is 0 or 1, and $R'$ is phenyl or phenyl substituted with 1 or 2 halogens, protected hydroxy, nitro, cyano, trifluoromethyl, $C_1$–$C_4$ alkyl, or $C_1$–$C_2$ alkoxy;
3. a group of the formula

in which $R'$ is as defined above and W is protected hydroxy, protected carboxy, or protected amino; or
c. an imidazolidinyl group of the formula

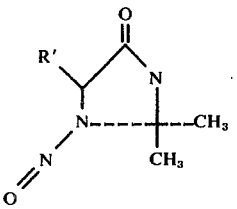

in which $R'$ is as defined above.

2. Process of claim 1, in which $R_1$ is $C_4$–$C_6$ tert-alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$ alkanoyloxymethyl, phenacyl, or p-halophenacyl.

3. Process of claim 2, in which $R_1$ is t-butyl, benzyl, p-nitrobenzyl, p-methoxybenzyl, benzhydryl, or 2,2,2-trichloroethyl.

4. Process of claim 1, in which R is an amido group of the formula

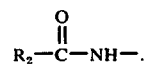

5. Process of claim 4, in which $R_2$ is a group of the formula $R'$—$(O)_m$—$CH_2$—.

6. Process of claim 5, in which $R'$ is phenyl.

7. Process of claim 4, in which $R_2$ is a group of the formula

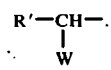

8. Process of claim 1, in which the reaction is carried out in the presence of a mixture of an aprotic inert organic solvent and a $C_1$–$C_4$ carboxylic acid.

9. Process of claim 8, in which the $C_1$–$C_4$ carboxylic acid is acetic acid.

10. Process of claim 1, in which the reaction is carried out at a temperature of from about −10° C. to about +25° C.

11. Process of claim 1, in which the mercuric ion precipitator is hydrogen sulfide.

* * * * *